US007016458B2

(12) United States Patent
Francke

(10) Patent No.: US 7,016,458 B2
(45) Date of Patent: Mar. 21, 2006

(54) TOMOGRAPHIC APPARATUS AND METHOD

(75) Inventor: Tom Francke, Sollentuna (SE)

(73) Assignee: Xcounter AB, Danderyd (SE)

( * ) Notice: Subject to any disclaimer, the term of this patent is extended or adjusted under 35 U.S.C. 154(b) by 244 days.

(21) Appl. No.: 10/750,941

(22) Filed: Jan. 5, 2004

(65) Prior Publication Data

US 2005/0117694 A1 Jun. 2, 2005

(30) Foreign Application Priority Data

Dec. 1, 2003 (SE) .................................. 0303226

(51) Int. Cl.
*A61B 6/00* (2006.01)
*G01N 23/02* (2006.01)
(52) U.S. Cl. .............................. 378/19; 378/4; 378/26; 378/62
(58) Field of Classification Search .................... 378/4, 378/15, 19, 21–27, 62, 901; 382/128
See application file for complete search history.

(56) References Cited

U.S. PATENT DOCUMENTS

| 4,736,396 A | 4/1988 | Boyd et al. |
| 5,430,783 A * | 7/1995 | Hu et al. ...................... 378/15 |
| 6,072,851 A | 6/2000 | Sivers |
| 6,118,125 A | 9/2000 | Carlson et al. |
| 6,337,482 B1 | 1/2002 | Francke |
| 6,373,065 B1 | 4/2002 | Francke et al. |
| 6,385,282 B1 | 5/2002 | Francke et al. |
| 6,414,317 B1 | 7/2002 | Francke et al. |
| 6,476,397 B1 | 11/2002 | Francke et al. |
| 6,477,223 B1 | 11/2002 | Francke |
| 6,518,578 B1 | 2/2003 | Francke et al. |
| 6,522,722 B1 | 2/2003 | Francke |
| 6,546,070 B1 | 4/2003 | Francke |
| 6,556,650 B1 | 4/2003 | Francke |
| 6,580,777 B1 | 6/2003 | Ueki et al. |
| 6,587,539 B1 * | 7/2003 | Oikawa ....................... 378/19 |
| 6,600,804 B1 | 7/2003 | Francke et al. |
| 6,627,897 B1 | 9/2003 | Francke et al. |
| 2002/0141531 A1 * | 10/2002 | Taguchi ....................... 378/19 |

FOREIGN PATENT DOCUMENTS

EP 1110505 A2 6/2001

* cited by examiner

*Primary Examiner*—Edward J. Glick
*Assistant Examiner*—Irakli Kiknadze
(74) *Attorney, Agent, or Firm*—Harness, Dickey & Pierce, PLC

(57) ABSTRACT

An apparatus for obtaining tomographic data of an object comprises a radiation source (50), a detector (42) comprising multiple line detectors (41), an object region (53) arranged in the radiation path between the source and the detector, and a device (54) for moving the source and detector relative the object, while each of the line detectors records multiple line images of radiation as transmitted through the object. The source emits radiation within a large angle to irradiate the object completely in one dimension (y), and the line detectors are sited in rows (71) and columns (72), wherein the line detectors in each row together define an opening angle ($\alpha$) large enough to detect the object completely in the dimension (y). The moving device is adapted to move the source and detector relative the object helically around a z axis to obtain tomographic data of the object, wherein the helical movement includes a rotation less than essentially one full revolution, and a distance along the z axis corresponding to a distance between two adjacent detectors in a column of the two-dimensional array.

44 Claims, 6 Drawing Sheets

TOMOGRAPHIC APPARATUS AND METHOD

TECHNICAL FIELD OF THE INVENTION

The present invention relates to an apparatus and a method for obtaining tomographic data of an object. The invention also relates to an apparatus and a method for obtaining tomographic, tomosynthesis, and still picture data of an object.

The invention is usable in a variety of fields including, computerized tomography (CT), tomosynthesis, radiography, medical radiology microscopy, and non-destructive testing.

DESCRIPTION OF RELATED ART AND BACKGROUND OF THE INVENTION

It is of great importance in many fields of technology to be capable of constructing a three-dimensional illustrative representation from a series of linear data resulting from various projections (i.e. line-of-sight measurements) taken of the matter one desires to reconstruct. For instance, by employing X-rays to provide a three-dimensional image of a human body, or part thereof, it is commonly known to pass X-rays through the body in a number of different directions and to measure the absorption of the X-rays.

Passing a planar beam of radiation through an object and detecting the amount of absorption within a cut of the object results in an essentially two-dimensional object being projected onto a one-dimensional image. Similarly, passing an unfocused beam of radiation through a three-dimensional body and detecting the amount of absorption within the body results in a three-dimensional body being projected onto a two-dimensional image. This results inevitably in superimposition of information and resulting loss of the information. Complex techniques have to be employed if one wishes to perform an examination with greater sensitivity to spatial variations in radiation absorption and with less severe superimposition effects.

In a computerized tomography (CT) examination method known as helical scanning a source of a radiation beam and a detector (photographic film or digital detector) are arranged for irradiating the object to be examined by the radiation beam, and for detecting the amount of radiation passed trough (i.e. not absorbed or scattered off) the object. The radiation source and the detector are revolved along a circular or other path around the body, while the object may be moved linearly in a direction orthogonal to the plane of the revolution, and readouts of the detector are performed at several positions of the revolution of the radiation source and the detector, and optionally at several positions of the linear movement of the object. Alternatively, the radiation source and the detector are revolved in a helical fashion, while the body is kept still. A three-dimensional reconstruction process of the body is then performed, wherein different structures of the body, e.g. soft tissue, bone, liquid-filled cavities, etc., become distinguishable as these structures show different absorption.

Detection devices for detecting the radiation in tomographic apparatuses of the kind depicted above include various kinds of scintillator-based detectors, gaseous ionization detectors, and solid-state detectors.

SUMMARY OF THE INVENTION

Drawbacks of prior art detection devices used in tomographic apparatuses are that they are costly and small, which implies an extensive scanning of a larger object. The detection devices have a limited sensitivity, possess relatively bad spatial resolution, and are noisy. Also, the prior art tomographic apparatuses involve a high dose to the patient.

Further, the tomographic apparatuses are typically employed for a single purpose, i.e. for CT, and thus the range of uses is limited to this.

It is therefore an object of the present invention to provide an apparatus and a method for obtaining tomographic data of a large object, such as a torso of a human being, which are affordable and which use a large-area detector, so that scanning can be made a very short distance while the object is imaged in a variety of directions to provide tomographic data sufficient for helical scanning CT.

It is a further object of the present invention to provide an apparatus and a method for obtaining tomographic, tomosynthesis, and still picture data of a large object, such as a torso of a human being, which are affordable and which use a large-area detector, so that scanning can be made while the object is imaged to provide data sufficient to perform helical scanning CT, tomosynthesis, and still picture visualization, respectively.

A further object of the present invention is to provide such apparatuses and methods, which are sensitive, effective, fast, accurate, reliable, flexible, easy to use, and of fairly low cost, and which can operate at very low X-ray fluxes and still provide for the recording of data with high spatial resolution.

These objects among others are, according to the present invention, attained by apparatuses and methods as claimed in the appended claims.

According to a first aspect of the invention an apparatus for obtaining tomographic data of an object is provided, the apparatus comprising a divergent radiation source provided for emitting radiation, a radiation detector comprising a two-dimensional array of line detectors, an object region arranged in the radiation path between the divergent radiation source and the radiation detector, and a device provided for moving the divergent radiation source and the radiation detector relative the object.

The radiation is emitted centered around an axis of symmetry, e.g. the x axis, and within a solid angle such that radiation is directed towards the full extension of the object at least in one dimension, which is perpendicular to the axis of symmetry, that is e.g. along the y axis.

Each of the line detectors has a detection-sensitive area directed towards the divergent radiation source and is provided for one-dimensional imaging of radiation entering the detection-sensitive area. The line detectors are sited in rows and columns in the two-dimensional array, wherein the line detectors of each row are sited edge-to-edge along a line, and are of a number and have each a length such that they together define a detecting opening angle large enough to detect the radiation directed towards the full extension of the object at least in one dimension.

The moving device is provided for moving the divergent radiation source and the radiation detector relative the object helically around a second axis being essentially perpendicular to the axis of symmetry and the one dimension, that is e.g. around the z axis, while each of the line detectors is adapted to record a plurality of line images of radiation as transmitted through the object to obtain tomographic data of the object. The helical movement includes preferably a rotation less than essentially the sum of one full revolution and the detecting opening angle, and a distance along the second axis corresponding to a distance between two adjacent detectors in a column of the two-dimensional array. The movement includes a rotation preferably essentially equal to one full revolution, more preferably essentially equal to the sum of one half revolution and the detecting opening angle, and most essentially equal to one half revolution. However, the rotation may be larger to obtain a better spatial resolution in the images reconstructed from the tomographic data.

According to a second aspect of the invention an apparatus for obtaining tomographic, tomosynthesis and still picture data of an object is provided, the apparatus comprising a divergent radiation source provided for emitting radiation, a radiation detector comprising a two-dimensional array of line detectors, an object region arranged in the radiation path between the divergent radiation source and the radiation detector, and a device provided for moving the divergent radiation source and the radiation detector relative the object.

The radiation is emitted centered around an axis of symmetry, e.g. the x axis, and within a solid angle such that radiation is directed towards the full extension of the object at least in one dimension, which is perpendicular to the axis of symmetry, that is e.g. along the y axis.

Each of the line detectors has a detection-sensitive area directed towards the divergent radiation source and is provided for one-dimensional imaging of radiation entering the detection-sensitive area. The line detectors are sited in rows and columns in the two-dimensional array, wherein the line detectors of each row are sited edge-to-edge along a line, and are of a number and have each a length such that they together define a detecting opening angle large enough to detect the radiation directed towards the full extension of the object at least in one dimension.

The moving device is provided to:
(i) move the divergent radiation source and the radiation detector relative the object helically around a second axis being essentially perpendicular to the axis of symmetry and the one dimension, while each of the line detectors is adapted to record a plurality of line images of radiation as transmitted through the object to obtain tomographic data of the object;
(ii) move the divergent radiation source and the radiation detector relative the object linearly in a plane perpendicular to the axis of symmetry, while each of the line detectors is adapted to record a plurality of line images of radiation as transmitted through the object to obtain tomosynthesis data of the object; and
(iii) move the divergent radiation source and the radiation detector relative the object linearly along the second axis a distance corresponding to a distance between two adjacent detectors in a column of the two-dimensional array, while each of the line detectors is adapted to record a plurality of line images of radiation as transmitted through the object to obtain still picture data of the object.

Preferably, the moving device of this apparatus is provided to move the divergent radiation source and the radiation detector relative the object along the second axis a distance corresponding to the full extension of the object in a second dimension, which is parallel with the second axis, to obtain the tomosynthesis data of the object. To this end the line detectors of the two-dimensional array are directed in directions, each of which defines a different angle with respect to the axis of symmetry. Advantageously, the different angles are distributed over an angular range of at least 5°, preferably at least 15°, and most preferably at least 25°.

Tomosynthesis data may alternatively be obtained by rotating the divergent radiation source and the radiation detector relative the object around the second axis less than half a revolution, while each of the line detectors is adapted to record a plurality of line images of radiation as transmitted through the object. Optionally, the scanning is performed helically with an angle of climb, which preferably is larger than the one used when obtaining tomographic data to scan the object.

Still preferably, the array of line detectors has a large area so that the distance from shoulder to shoulder of a human being, preferably an adult human being, can be covered by a single one of the rows of line detectors. Thus, the two-dimensional array of line detectors measures at least 50 cm×25 cm, and preferably about 100 cm×50 cm, and comprises at least 10×50, or even 20×100 line detectors.

The line detectors are each advantageously a detector, which is direction sensitive to avoid the need of a scattering rejection collimator in front the line detector. One preferred example of such a detector is the gaseous-based ionization detector, wherein electrons freed as a result of ionization by radiation are accelerated in a direction essentially perpendicular to the direction of that radiation, optionally avalanche amplified, and subsequently detected. Such line detectors are quite inexpensive to manufacture and can accordingly be afforded to be provided in the number specified above to cover the area desired.

An advantage of the apparatus according to the second aspect of the present invention is that the radiologist has an option to either record tomographic data for CT using a relatively higher dose to the object (due to many detections/projections), or to record tomosynthesis data using a relatively lower dose to the object (thanks to fewer detections/projections).

Further characteristics of the invention, and advantages thereof, will be evident from the detailed description of preferred embodiments of the present invention given hereinafter and the accompanying FIGS. 1–5, which are given by way of illustration only, and thus are not limitative of the present invention.

BRIEF DESCRIPTION OF THE DRAWINGS

FIG. 4b illustrates schematically, in a front view with an entrance window partly removed, the line detector of FIG. 4a.

DETAILED DESCRIPTION OF PREFERRED EMBODIMENTS

Figure 1A:
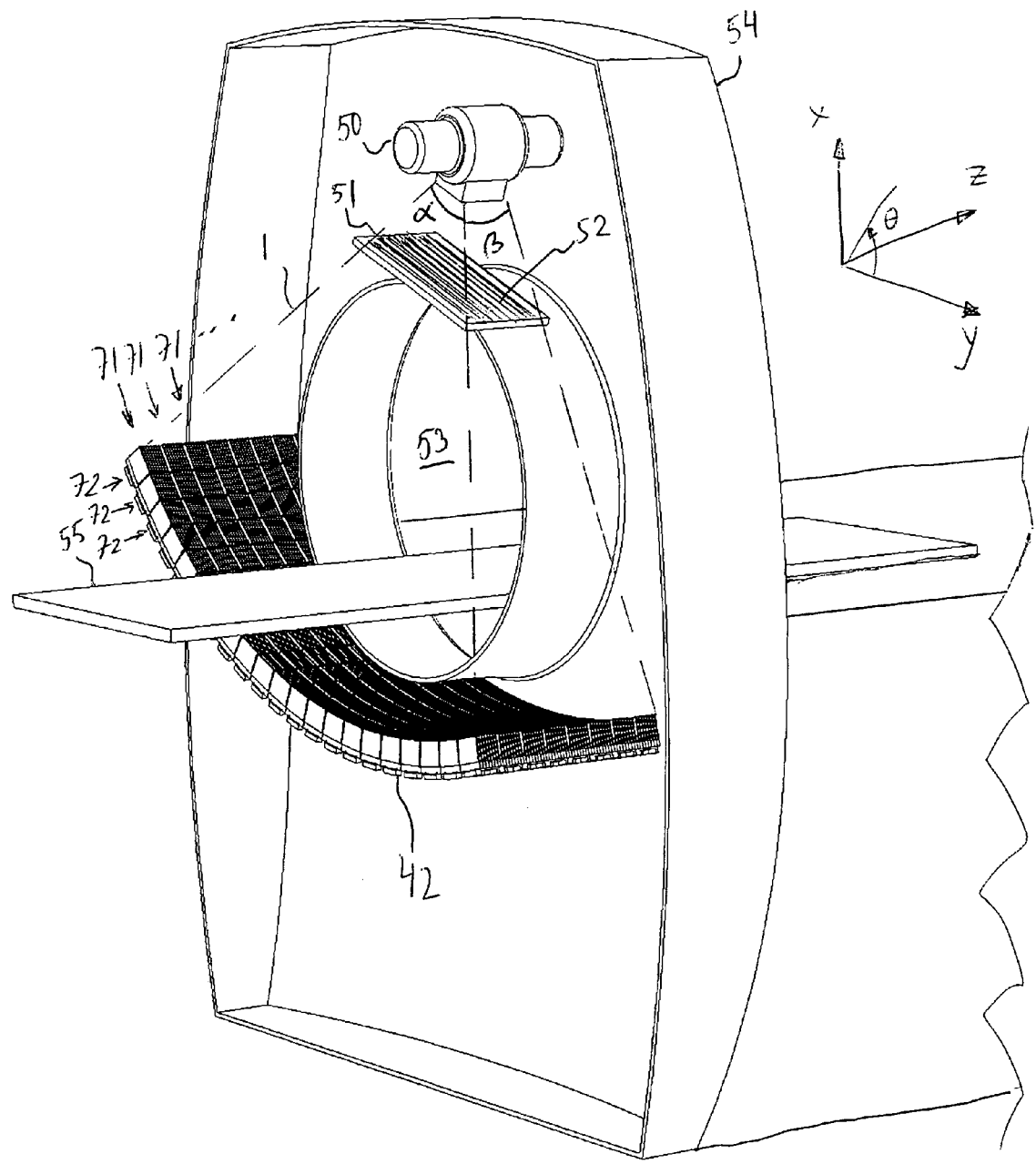
FIGS. 1a–b illustrates schematically, in perspective and views, a computerized tomography apparatus for medical radiology applications according to an embodiment of the invention.
Figure 1B:
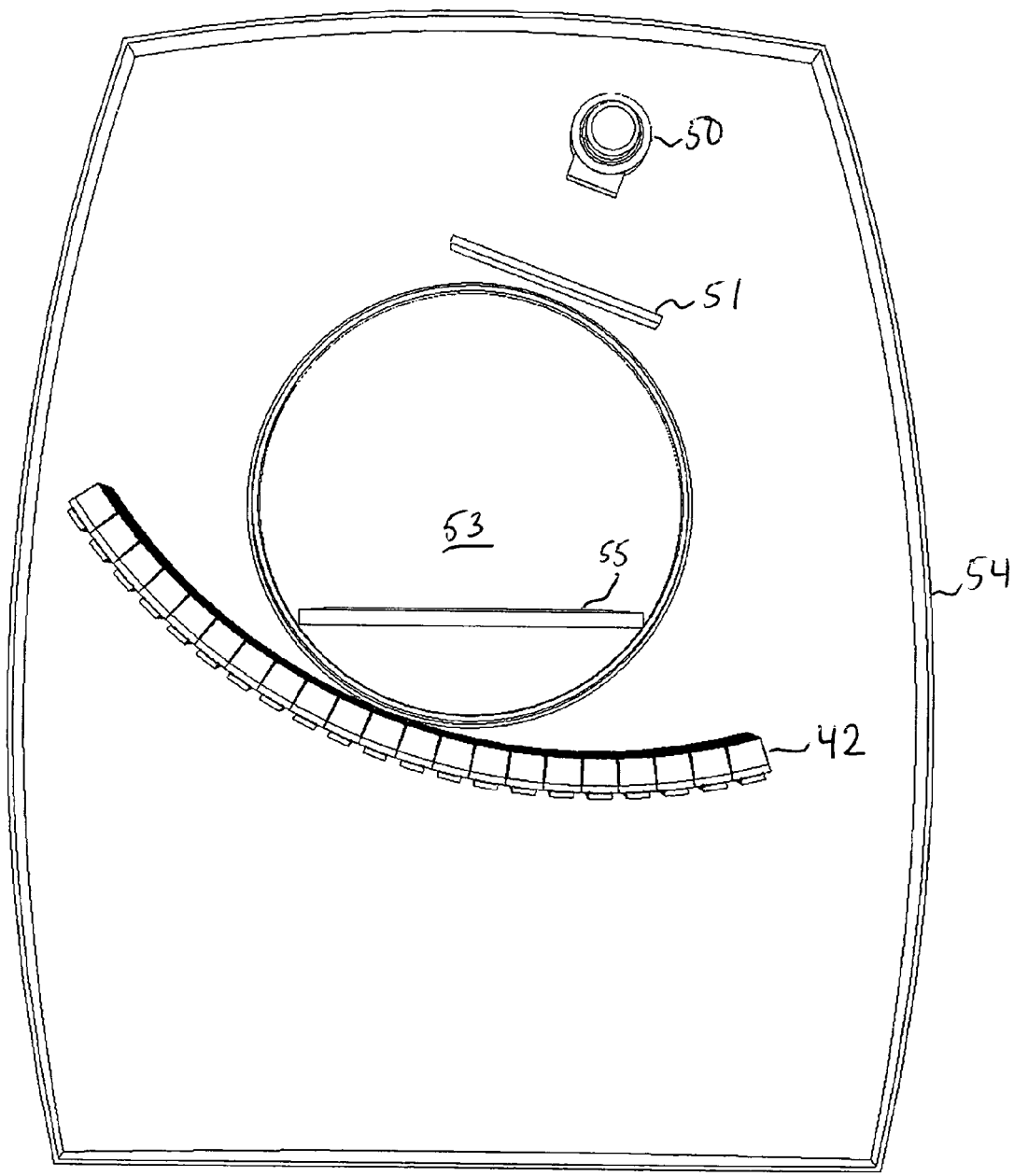

With reference to FIGS. 1a–b, which schematically illustrates a computerized tomography apparatus 54 for medical radiology applications, a preferred embodiment of the present invention will be described. The tomographic apparatus 54 comprises a divergent radiation source 50, which emits radiation 1 centered around an axis of symmetry, which coincides with the x axis as illustrated. The radiation 1 is emitted with a solid angle defined by the planar angles $\alpha$ in the xy plane and $\beta$ in the xz plane to impinge on a radiation detector 42 comprising a curved two-dimensional array of line detectors, which are sited in rows 71 and columns 72, wherein the line detectors of each row 71 are sited edge-to-edge along a line. If the line detectors are capable of detecting at their far extremes, a row of line detectors detect simultaneously a long continuous one-dimensional image of radiation. If the line detectors are not capable of detecting at their far extremes, the one-dimensional image of radiation contains unmeasured areas between areas covered by two adjacent line detectors of the row.

Figure 2:
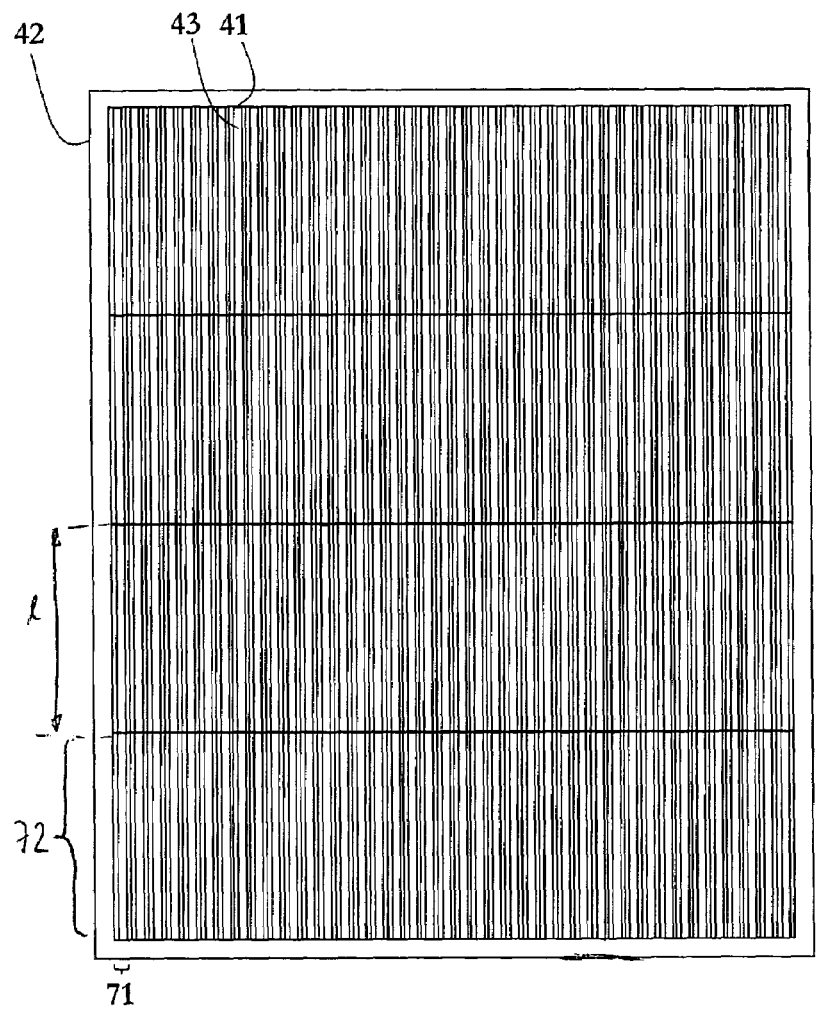
FIG. 2 illustrates schematically, in a top view, a two-dimensional array of line detectors for use in the tomography apparatus of FIGS. 1a–b.

The detector array, of which an example is schematically illustrated in a top view in FIG. 2, comprises a large number of line detectors 41, each having a detection-sensitive area 43 directed towards the divergent radiation source 50 and is provided for one-dimensional imaging of radiation entered into the detection-sensitive area 43. To this end, each of the line detectors 41 is directed in a direction, which defines a different angle with respect to the axis of symmetry, or the x axis; and is direction sensitive. Hereby, the need of scattering rejection collimators in front the detectors 41 is avoided.

In the radiation path between the divergent radiation source 50 and the radiation detector 42, a region 53 is provided for housing an object to be examined. The object, which typically is a human being, is arranged onto a table 55, which is movable in and out of the region 53 along the z axis.

Figure 3:
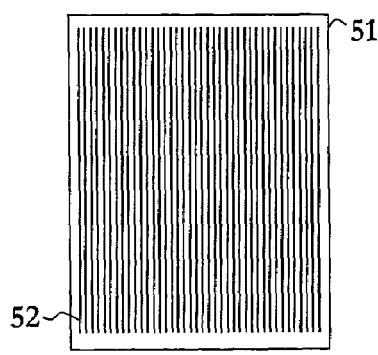
FIG. 3 illustrates schematically, in a top view, a collimator for use in the tomography apparatus of FIGS. 1a–b.

If the object is a living organism it may be advantageous to arrange a collimator 51 in the radiation path between the radiation source 50 and the region 53, where the collimator 51 prevents radiation, which is not directed towards the line detectors, from impinging on the object, thereby reducing the radiation dose to the object. To this end the collimator 51, which is schematically illustrated in a top view in FIG. 3, is of a radiation opaque material and comprises a number of elongated slits 52, which corresponds to the number of detection rows 71 in the two-dimensional array of line detectors 41, wherein each of the slits is aligned with a respective one of the rows 71 of line detectors. Thus, the object is only irradiated by radiation, which actually contributes to the detection.

The tomographic apparatus 54 comprises an integral moving mechanism or device for moving the radiation source 50, the collimator 51 and the radiation detector 42 relative the object to be examined. The moving mechanism may preferably be capable of rotating the radiation source 50, the collimator 51 and the radiation detector 42 in the xy plane, e.g. in the $\theta$ direction if cylindrical coordinates are used, whereas the object arranged may be moved linearly in the z direction, by means of moving the table 55, on which the object is arranged. The simultaneous rotational movement of the radiation source 50, the collimator 51 and the radiation detector 42 in the xy plane, and translative movement of the object in the z direction result in a helical movement of the radiation source 50, the collimator 51 and the radiation detector 42 relative the object. It shall be appreciated by the man skilled in the art that the moving mechanism of the tomographic apparatus 54 of the present invention may be realized in other manner as long as it provides for a helical, and optionally a linear movement, of the radiation source 50, the collimator 51 and the radiation detector 42 relative the object.

While the radiation source 50, the collimator 51 and the radiation detector 42 are moved relative the object, each of the line detectors 41 is adapted to record a plurality of line images of radiation as transmitted through the object, to achieve a scanning measurement of the object.

According to the present invention, the radiation source 50 is provided for emitting radiation within an angle $\alpha$ in the xy plane such that radiation is directed towards the full extension of the object at least in one dimension, e.g. along the y axis, which is perpendicular to the axis of symmetry or the x axis, and the line detectors 41 of the two-dimensional array of line detectors are of a number and have each a length l such that they together define an detector opening angle $\alpha$ large enough to detect the radiation directed towards the full extension of the object in the dimension indicated above, e.g. along the y axis. How large area that has to be covered, how large line detectors have to be used and how many of them are needed are questions discussed more in detail below.

Still according to the present invention, the moving mechanism or device of the tomographic apparatus 54 is provided to move the radiation source 50, the collimator 51 and the radiation detector 42 relative the object helically around the z axis, being essentially perpendicular to the axis of symmetry or the x axis, and the y axis, to obtain tomographic data of the object, wherein the helical movement includes a rotation less than essentially the sum of one half revolution and the opening angle $\alpha$ of the radiation detector 42 in the xy plane, and a distance along the z axis, which corresponds to a distance between two adjacent detectors in a column of the two-dimensional array. Hereby, sufficient tomographic data is achieved for performing a reconstruction process used for helical scanning CT.

Preferably, the divergent radiation source 50 is provided for emitting radiation within an angle $\beta$ in the xz plane such that radiation is directed towards the full extension of the object in the z direction, and the line detectors of each column 72 are sited with a distance from each other and are of a number such that they are together capable of detecting the radiation directed towards the full extension of the object in z direction.

The line detectors 41 of each column 72 should not be separated by a distance larger than about 28 times the spatial resolution of the line detectors in the z direction. Thus, provided that the spatial resolution in the z direction is about 100–500 microns, the distance between the line detectors 41 in each column 72 should not be more than about 3–15 mm. In an alternative version the line detectors 41 are, as being illustrated in FIG. 2, sited up against each other to provide a dense two-dimensional array of line detectors.

Alternatively, the helical scanning may be performed by a including a rotation corresponding to at least the sum of half a revolution and the opening angle $\alpha$ of the radiation detector 42 in the xy plane, e.g., or the sum of two full revolutions and the opening angle $\alpha$, etc.

It shall be noted that the larger the rotation in the helical movement is, the better the spatial resolution in a three-dimensional image reconstructed from the tomographic data using available reconstructions techniques is (due to a larger amount of tomographic data), but to the cost of increased detection time and increased radiation dose to the object.

For instance, if the distance between each two neighboring detection rows 71 in the two-dimensional array of line detectors 41 are separated by 3 mm, a spatial resolution in the z direction of about 1.5 mm is achievable if the helical scanning is performed half a revolution plus the opening angle α, whereas a spatial resolution in the z direction of about 0.75 mm is achievable if the helical scanning is performed a full revolution plus the opening angle α.

This means that the helical movement may include a rotation, which corresponds to a predetermined required spatial resolution in the image reconstructed from the tomographic data as imposed by e.g. a physician or radiologist depending on the examination to be performed, on a maximum allowable radiation dose exposed to the object and/or on a maximum allowable detection time.

The tomographic apparatus 54 with the large area detector may be modified to be capable of detecting radiation for different applications, i.e. for obtaining tomographic, tomosynthesis, and still picture data of the object. Thus the moving mechanism or device of the tomographic apparatus 54 may be provided to:

(i) move the radiation source 50, the collimator 51, and the radiation detector 42 relative the object helically around the z axis to obtain tomographic data of the object;

(ii) move the radiation source 50, the collimator 51, and the radiation detector 42 relative the object linearly in a plane yz perpendicular to the axis of symmetry or the x axis to obtain tomosynthesis or laminographic data of the object; and (iii) move the radiation source 50, the collimator 51 and the radiation detector 42 relative the object linearly along the z axis a distance corresponding to at least a distance between two adjacent detectors 41 of a column of the two-dimensional array to obtain still picture data of the object.

In order to obtain tomosynthesis or laminographic data it is important that the line detectors 41 of the two-dimensional array are directed in different directions with respect to the axis of symmetry or the x axis, or with respect to the y axis. Preferably, the directions defines different angles with respect to the x axis, wherein the different angles are distributed over an angular range of at least 5°, preferably at least 15°, and most preferably at least 25°.

The moving mechanism or device is advantageously provided to move the radiation source 50, the collimator 51 and the radiation detector 42 relative the object along the x axis a distance corresponding to the full extension of the object in the z dimension or direction to obtain the tomosynthesis data of the object. Thus, a plurality of two-dimensional images at different angles are produced in a single scan, which reduces the detection time by a factor corresponding to the number of two-dimensional images produced.

When obtaining still picture data of the object, the moving mechanism or device may be provided to move the radiation source 50, the collimator 51 and the radiation detector 42 relative the object linearly along the z axis a distance longer than a distance between two adjacent detectors 41 in one of the columns 72 of the two-dimensional array to obtain oversampled still picture data of the object. By oversampling, the effect of any movement blurredness can be further reduced, i.e. by recording a plurality of images at each location such that each portion of a two-dimensional image of the object formed, is built up by contributions from several line images recorded at different times, where the object is most probably not moving during all of the several line image recordings. The overlap in the scan can further be used to avoid any measurement problems at the beginning and/or at the final of the scan.

If the scanning is performed a total distance, which is at least twice the distance between each two adjacent line detectors 41 in a column, more than one line detector 41 is used to scan the same area of the object and any measurement problems due to individual readout strips being damaged and out of operation can be avoided.

The radiation detector 42 is, as have been indicated above, a large area detector. Preferably, the radiation detector 42 is large enough to instantaneously detect an object entirely in the y direction, where the object measures at least 30 cm, more preferably at least 40 cm, and most preferably at least 50 cm. Naturally, the radiation source 50 have to be provided to emit radiation within a solid angle to cover such an object, and the collimator 51 has to be designed to allow radiation that is directed towards the line detectors 41 of the radiation detector 42 to pass through. If the object is a human being the full extension of the human being in the y direction corresponds to the distance from shoulder to shoulder.

The two-dimensional array of line detectors may measure at least 50 cm×25 cm, preferably at least 75 cm×40 cm, and most preferably at least about 100 cm×50 cm in the y and z directions. Each column 72 of the two-dimensional array of line detectors may comprises at least 5 line detectors, preferably at least 10 line detectors, and most preferably at least about 20 line detectors, and each column 72 may comprise at least 25 line detectors, preferably at least 50 line detectors, and most preferably at least about 100 line detectors in each column.

Further, the apparatus of the present invention may be equipped with any of a PET scanner, an ultrasound examination apparatus, and a SPECT scanner to provide measurements, which may serve as a complement for diagnosis.

Figure 4A:
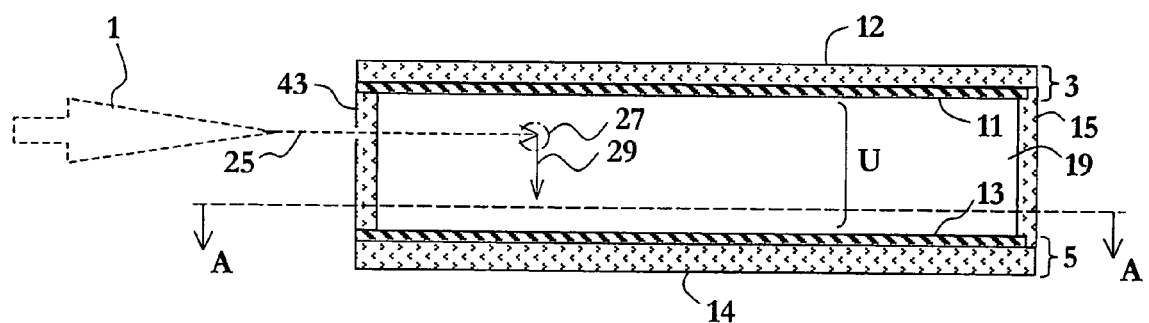
FIG. 4a illustrates schematically, in a cross-sectional side view, a line detector for use in the two-dimensional array of line detectors of FIG. 2.
Figure 4B:
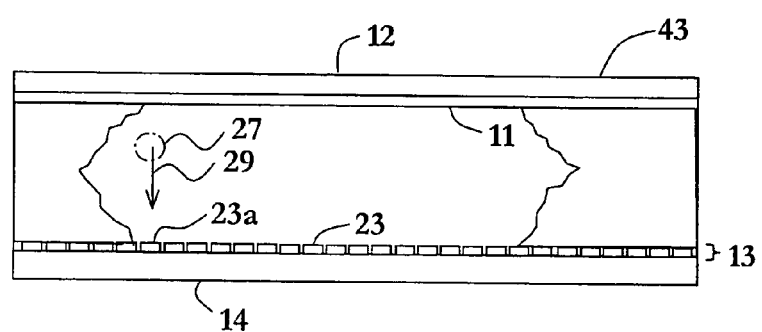
Figure 4C:
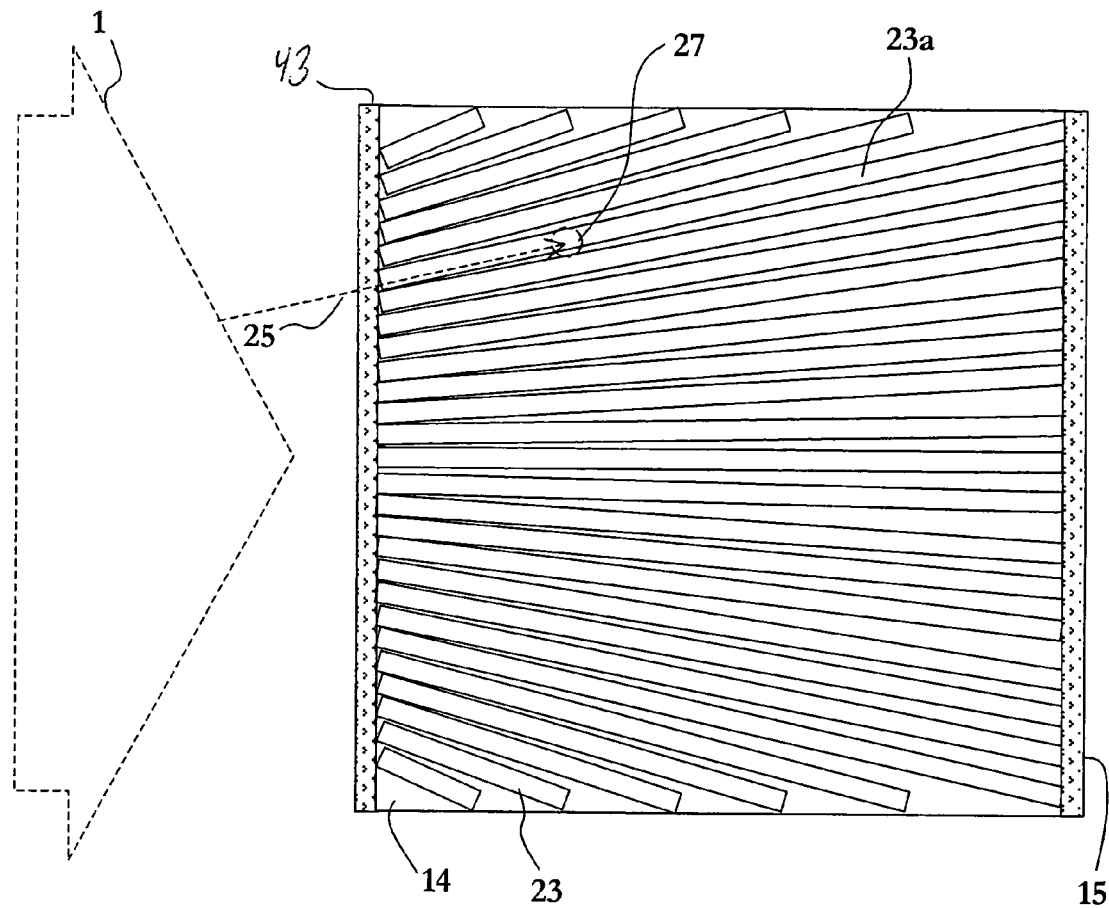
FIG. 4c illustrates schematically a cross-sectional view of the line detector of FIG. 4a as taken along the line A—A.

With reference to FIGS. 4*a–c*, which are a cross-sectional side view, a front view with entrance window portions removed, and a cross-sectional top view, respectively, of a line detector for use in the tomographic apparatuses of the present invention, this line detector will briefly be overviewed.

The line detector is oriented so that radiation 1 can enter sideways between a cathode arrangement 3 and an anode arrangement 5. An entrance window 43 is provided at the front of the line detector to form an entrance for the radiation 1 to the line detector. The entrance window 43 is of a plastic or carbon fiber material.

Each of the electrode arrangements 3, 5 includes an electrically conducting electrode layer 11, 13 supported by a respective dielectric substrate 12, 14, wherein the arrangements are oriented so that the cathode 11 and anode 13 layers are facing each other. Preferably, the electrode arrangements 3 and 5 are planar, rectangular and parallel to each other.

The entrance window 43 and the back wall 15 are provided to keep the electrodes arrangements 3, 5 apart.

The electrode arrangements 3 and 5 are arranged within an external gas-tight casing (not illustrated), which is filled with an ionizable gas or gas mixture 19, e.g. comprising krypton, carbon dioxide and/or xenon. The gas may be under pressure, preferably in a range 1–20 atm.

A high voltage DC supply unit (not illustrated) is provided for the purpose of holding the cathode 11 and the anode 13 at suitable electric potentials to create an electric field within the inter-electrode confinement 19 for drift, and optionally amplification, of electrons and ions therein. Conveniently, the cathode 11 is held, during use, at a negative voltage $-V_1$, whereas the anode 13 is grounded.

Further, the line detector comprises a readout arrangement for detection of electrons drifted towards the anode 13 and/or ions drifted towards the cathode 11. The readout arrangement is preferably comprised of the anode arrangement 5 itself.

To provide for one-dimensional imaging capabilities, the anode/readout layer 13 is comprised of an array of conductive or semiconducting elements or strips 23 arranged side by side and electrically insulated from each other on the dielectric substrate 14. To compensate for parallax errors in detected images, and to thereby provide for an increased spatial resolution, the anode/readout strips extend essentially in directions parallel to the direction of incident photons of the radiation 1 at each location. Each of the anode/readout strips is preferably connected to a readout and signal-processing device (not illustrated), whereupon the signals from each strip can be processed separately. As the strips also constitute the anode suitable couplings for separation are needed.

It shall be appreciated that the distance between the electrode layers 11 and 13 is strongly exaggerated in FIGS. 1 and 2 for illustrative purposes. As an example geometry the line detector may be 40 mm wide or long (denoted by 1 in FIG. 4b), 2 mm thick and 35 mm deep, whereas the inter-electrode distance may be between 0.05 and 2 mm. Each readout strip 23 may be 10 $\mu$m–2 mm wide, which implies that several hundred or thousand strips may be arranged side by side in a single line detector, i.e. much more than illustrated.

In operation, X-rays enter the line detector through the collimator slit, parallel and close to the cathode arrangement 3. The X-rays will interact with the gas in the line detector according to an exponential probability distribution where the majority of the X-rays convert early in the gas volume. The average interaction length may typically be 10–100 mm.

At an interaction, an X-ray photon 25 transmits its energy to an electron in a gas atom, which is released from the atom through processes known as photo effect, Compton scattering and/or Auger effect. This electron travels through the gas and collides with new gas atoms, thereby liberating more electrons until it eventually has lost all its energy and stops. In this process a cloud 27 typically of about thousand electrons is created.

By applying a voltage U between the cathode 11 and the anode 13, these electrons are attracted towards the anode in a direction 29 (vertical in FIGS. 1–2), which is essentially perpendicular to the incoming X-ray photon trajectory. If the electric field applied is strong enough, the electrons gain enough energy to knock out further electrons from the gas, which in turn are accelerated, and knock out yet further electrons in an avalanche process. This process is known as gaseous avalanche amplification. At the anode, the electrons induce electric signals in the strip 23a nearest to the cloud 27.

The electronic signal is detected by the readout electronics connected to the strip. In the electronics, the signal is amplified and compared with a threshold voltage. If the signal exceeds the threshold voltage, a counter specific for this strip is activated and adds one to a previous value stored. In this way, the number of X-rays impinging above each anode strip is counted. The method is called photon counting.

It has been found quite recently that the line detector of FIGS. 4a–c is extremely direction sensitive. Only collimated photons entering the line detector in a very thin plane closest to the cathode electrode 11 will be amplified sufficiently to essentially contribute to the signal as detected. Thus, the line detector does not need any kind of scattering rejection collimator in front the detector.

The gaseous-based line detector described above is reasonably priced, and thus it is very suitable to be used in the present invention. As many as 1000 or more of the line detector may conveniently be arranged together in a gas-tight casing capable of being filled with an ionizable gas to form the two-dimensional array of line detectors as illustrated in FIGS. 1a–b.

It shall be noted that the line detector of FIGS. 4a–c is capable of detecting along its complete width or length l as the multiple readout strips 23 are arranged from side to side (see FIG. 4c), and the line detector lacks sidewalls. In this respect, the entrance window 43 has to be sufficiently transparent to the incident radiation to obtain a sufficiently high radiation flux within the detector, but sufficiently strong to keep the electrodes apart also at high voltages (when the electrostatic attraction forces may be high).

Figure 5A:
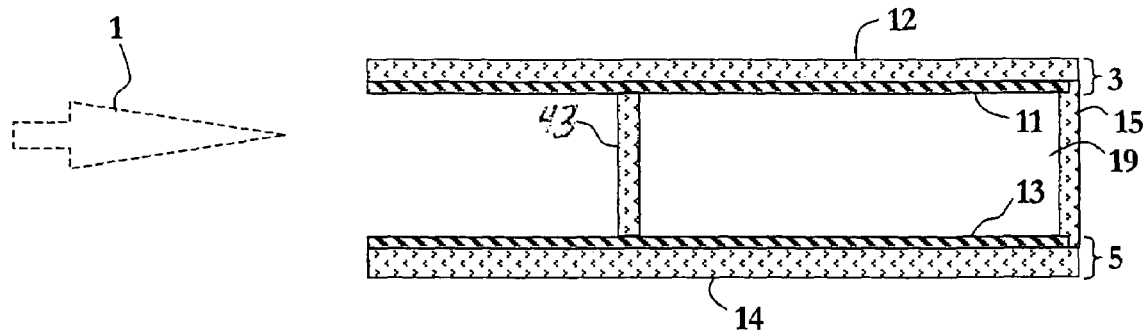
FIGS. 5a–b illustrate schematically, in cross-sectional side views, alternative line detectors for use in the two-dimensional array of line detectors of FIG. 2.

In FIG. 5a an alternative line detector for use in the present invention is illustrated, the line detector being identical with the line detector of FIGS. 4a–c apart from that the window 43 is arranged a certain distance from the entrance of the line detector, that is the electrode arrangements 3, 5 are extending on both sides of the window 43. Since the absorption in the ionizable gas within the detector is exponentially decreasing, the total absorption in the window 43 becomes lower, the more the window 43 is distanced from the entrance of the line detector. On the other hand, the support for keeping the electrode arrangements 3, 5 apart in the front end of the line detector is reduced.

Figure 5B:
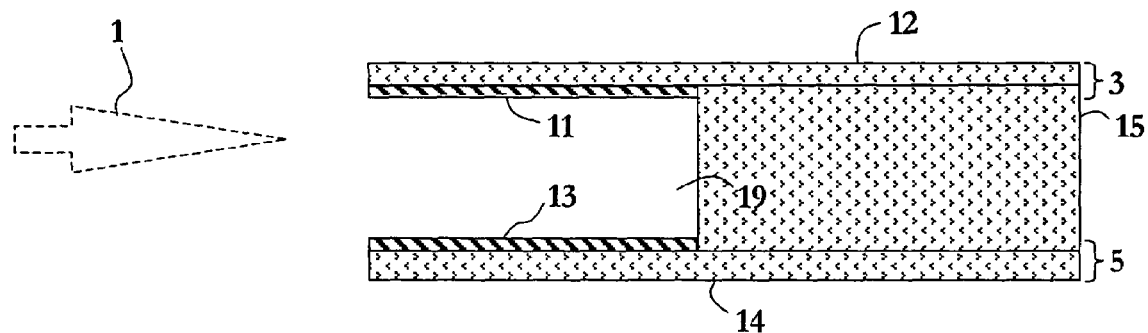

In FIG. 5b yet an alternative line detector for use in the present invention is illustrated. This preferred embodiment lacks the window 43. Instead, the back wall 15 is a structure that extends considerably in the direction of the incident radiation 1 to give support to the electrode arrangements 3, 5.

In other respects this embodiment does not differ from the embodiments disclosed in FIGS. 4a–c and 5a.

Other line detectors for use in the present invention are those described in the following U.S. Patents by Tom Francke et al. and assigned to XCounter AB of Sweden, which patents are hereby incorporated by reference: U.S. Pat. Nos. 6,118,125; 6,373,065; 6,337,482; 6,385,282; 6,414,317; 6,476,397; 6,477,223; 6,518,578; 6,522,722; 6,546,070; 6,556,650; 6,600,804; and 6,627,897.

Still alternatively, the line detectors used in the present invention may each be any of a diode array, a semiconductor PIN-diode array, a scintillator-based array, a CCD array, a TFT- or CMOS-based detector, or a liquid detector.

What is claimed is:

1. An apparatus for obtaining tomographic data of an object comprising:
    a divergent radiation source provided for emitting radiation centered around an axis of symmetry;
    a radiation detector comprising a two-dimensional array of line detectors, each having a detection-sensitive area directed towards the divergent radiation source and being provided for one-dimensional imaging of radiation entering said detection-sensitive area;
    a region arranged in the radiation path between said divergent radiation source and said radiation detector provided for housing said object; and
    a device provided for moving said divergent radiation source and said radiation detector relative said object, while each of said line detectors is adapted to record a plurality of line images of radiation as transmitted through said object, wherein:

said divergent radiation source is provided for emitting radiation within a solid angle such that radiation is directed towards the full extension of said object at least in a first dimension, which is perpendicular to said axis of symmetry;

the line detectors of said two-dimensional array of line detectors are sited in rows and columns, wherein the line detectors of each row are sited edge-to-edge along a line, and are of a number and have each a length such that they together define an opening angle large enough to detect said radiation directed towards the full extension of said object in said first dimension; and said moving device is provided for moving said divergent radiation source and said radiation detector relative said object helically around a second axis being essentially perpendicular to said axis of symmetry and the direction of said first dimension, to obtain tomographic data of said object, wherein said helical movement includes a rotation less than essentially the sum of one full revolution and said opening angle, and a distance along said second axis corresponding to a distance between two adjacent detectors in a column of said two-dimensional array.

2. The apparatus of claim 1 wherein said rotation is essentially equal to the sum of one half revolution and said opening angle.

3. The apparatus of claim 1 wherein said divergent radiation source is provided for emitting radiation within a solid angle such that radiation is directed towards the full extension of said object in a second dimension, which is perpendicular to said first dimension and to said axis of symmetry;

the line detectors of each column are sited with a distance from each other and are of a number such that they are together capable of detecting said radiation directed towards the full extension of said object in said second dimension.

4. The apparatus of claim 1 wherein the full extension of said object in said first dimension measures at least 30 cm.

5. The apparatus of claim 1 wherein the full extension of said object in said first dimension measures at least 40 cm.

6. The apparatus of claim 1 wherein the full extension of said object in said first dimension measures at least 50 cm.

7. The apparatus of claim 1 wherein the full extension of said object in said first dimension corresponds to the distance from shoulder to shoulder of a human being.

8. The apparatus of claim 1 wherein said two-dimensional array of line detectors measures at least 50 cm×25 cm.

9. The apparatus of claim 1 wherein said two-dimensional array of line detectors measures at least 75 cm×40 cm.

10. The apparatus of claim 1 wherein said two-dimensional array of line detectors measures at least 100 cm×50 cm.

11. The apparatus of claim 1 wherein each row of said two-dimensional array of line detectors comprises at least 5 line detectors.

12. The apparatus of claim 1 wherein each row of said two-dimensional array of line detectors comprises at least 10 line detectors.

13. The apparatus of claim 1 wherein each row of said two-dimensional array of line detectors comprises at least 20 line detectors.

14. The apparatus of claim 1 wherein each column of said two-dimensional array of line detectors comprises at least 25 line detectors.

15. The apparatus of claim 1 wherein each column of said two-dimensional array of line detectors comprises at least 50 line detectors.

16. The apparatus of claim 1 wherein each column of said two-dimensional array of line detectors comprises at least 100 line detectors.

17. The apparatus of claim 1 wherein said two-dimensional array of line detectors is curved.

18. The apparatus of claim 1 comprising a collimator arranged in the radiation path between said radiation source and said region, said collimator preventing radiation, which is not directed towards said line detectors, from impinging on said object, thereby reducing the radiation dose to said object.

19. The apparatus of claim 1 wherein said line detectors are each a detector, which is direction sensitive to avoid the need of a scattering rejection collimator in front the detector.

20. The apparatus of claim 19 wherein said line detectors are each a detector, which is capable of detecting along its complete length.

21. The apparatus of claim 1 wherein said divergent radiation source is an X-ray source; and said line detectors are each a gaseous-based ionization detector, wherein electrons freed as a result of ionization by radiation are accelerated in a direction essentially perpendicular to the direction of that radiation.

22. The apparatus of claim 21 wherein said gaseous-based ionization detector is an electron avalanche detector.

23. The apparatus of claim 1 wherein said line detectors are each any of a diode array, a semiconductor PIN-diode array, a scintillator-based array, a CCD array, a TFT- or CMOS-based detector, or a liquid detector.

24. The apparatus of claim 1 wherein said apparatus further comprises any of a PET scanner, an ultrasound examination apparatus, and a SPECT scanner.

25. The apparatus of claim 1 wherein said helical movement includes a rotation of at least the sum of one full revolution and said opening angle.

26. An apparatus for obtaining tomographic, tomosynthesis, and still picture data of an object comprising:

a divergent radiation source provided for emitting radiation centered around an axis of symmetry;

a radiation detector comprising a two-dimensional array of line detectors, each having a detection-sensitive area directed towards the divergent radiation source and being provided for one-dimensional imaging of radiation entering said detection-sensitive area;

a region arranged in the radiation path between said divergent radiation source and said radiation detector provided for housing said object; and a device provided for moving said divergent radiation source and said radiation detector relative said object, while each of said line detectors is adapted to record a plurality of line images of radiation as transmitted through said object, wherein:

said divergent radiation source is provided for emitting radiation within a solid angle such that radiation is directed towards the full extension of said object at least in a first dimension, which is perpendicular to said axis of symmetry;

the line detectors of said two-dimensional array of line detectors are sited in rows and columns, wherein the line detectors of each row are sited edge-to-edge along a line, and are of a number and have each a length such that they are together capable of detecting said radiation directed towards the full extension of said object in said first dimension; and said moving device is provided for moving said divergent radiation source and said radiation detector relative said object helically around a second axis being essentially perpendicular to said axis of symmetry and the direction of said first dimension, to obtain tomographic data of said object;

moving said divergent radiation source and said radiation detector relative said object linearly in a plane perpendicular to said axis of symmetry to obtain tomosynthesis data of said object; and moving said divergent radiation source and said radiation detector relative said object linearly along said second axis a distance corresponding to a distance between two adjacent detectors in a column of said two-dimensional array to obtain still picture data of said object.

27. The apparatus of claim 26 wherein said wherein said helical movement includes a rotation less than essentially the sum of one full revolution and said opening angle, and a distance along said second axis corresponding to a distance between two adjacent detectors in a column of said two-dimensional array.

28. The apparatus of claim 27 wherein said rotation is essentially equal to the sum of one half revolution and said opening angle.

29. The apparatus of claim 26 wherein said line detectors of said two-dimensional array are directed in directions, each of which defines a different angle with respect to said axis of symmetry.

30. The apparatus of claim 29 wherein the different angles are distributed over an angular range of at least 5°.

31. The apparatus of claim 29 wherein the different angles are distributed over an angular range of at least 15°.

32. The apparatus of claim 29 wherein the different angles are distributed over an angular range of at least 25°.

33. The apparatus of claim 26 wherein said moving device is provided for moving said divergent radiation source and said radiation detector relative said object along said second axis a distance corresponding to the full extension of said object in a second dimension, which is perpendicular to the direction of said first dimension and to said axis of symmetry, to obtain said tomosynthesis data of said object.

34. The apparatus of claim 26 wherein said moving device is provided for moving said divergent radiation source and said radiation detector relative said object rotationally around said second axis, to obtain tomosynthesis data of said object, wherein said helical movement includes a rotation less than essentially the sum of one half revolution and said opening angle.

35. The apparatus of claim 26 wherein said moving device is provided for moving said divergent radiation source and said radiation detector relative said object linearly along said second axis a distance longer than a distance between two adjacent detectors in a column of said two-dimensional array to obtain oversampled still picture data of said object.

36. The apparatus of claim 26 wherein said divergent radiation source is provided for emitting radiation within a solid angle such that radiation is directed towards the full extension of said object in a second dimension, which is perpendicular to said first dimension and to said axis of symmetry;

the line detectors of each column are sited with a distance from each other and are of a number such that they are together capable of detecting said radiation directed towards the full extension of said object in said second dimension.

37. The apparatus of claim 36 wherein the line detectors of each column are sited up against each other to provide a dense two-dimensional array of line detectors.

38. A method for obtaining tomographic data of an object comprising:

emitting a divergent radiation beam centered around an axis of symmetry;

passing said emitted radiation through said object; and detecting said emitted radiation as a plurality of line images after having passed through said object by a radiation detector comprising a two-dimensional array of line detectors, the line detectors being sited in rows and columns, wherein the line detectors of each row are sited edge-to-edge along a line, and each of said line detectors has a detection-sensitive area directed towards the divergent radiation source and is provided for one-dimensional imaging of radiation entering said detection-sensitive area, while said divergent radiation source and said radiation detector are moved relative said object, wherein:

said divergent radiation beam is passed through the full extension of said object at least in a first dimension, which is perpendicular to said axis of symmetry;

radiation of said divergent radiation beam passed through the full extension of said object in said first dimension is detected by one of said rows of line detectors instantaneously; and said divergent radiation source and said radiation detector are moved relative said object helically around a second axis being essentially perpendicular to said axis of symmetry and the direction of said first dimension, while detecting by said radiation detector to obtain tomographic data of said object, wherein said helical movement includes a rotation less than essentially the sum of one full revolution and said opening angle, and a distance along said second axis corresponding to a distance between two adjacent detectors in a column of said two-dimensional array.

39. A method for obtaining tomographic, tomosynthesis, and still picture data of an object comprising:

emitting a divergent radiation beam centered around an axis of symmetry;

passing said emitted radiation through said object; and detecting said emitted radiation as a plurality of line images after having passed through said object by a radiation detector comprising a two-dimensional array of line detectors, the line detectors being sited in rows and columns, wherein the line detectors of each row are sited edge-to-edge along a line, and each of said line detectors has a detection-sensitive area directed towards the divergent radiation source and is provided for one-dimensional imaging of radiation entering said detection-sensitive area, while said divergent radiation source and said radiation detector are moved relative said object, wherein:

said divergent radiation beam is passed through the full extension of said object at least in a first dimension, which is perpendicular to said axis of symmetry;

radiation of said divergent radiation beam passed through the full extension of said object in said first dimension is detected by one of said rows of line detectors instantaneously;

said divergent radiation source and said radiation detector are moved relative said object helically around a second axis being essentially perpendicular to said axis of symmetry and the direction said first dimension, while detecting by said radiation detector, to obtain tomographic data of said object;

said divergent radiation source and said radiation detector are moved relative said object linearly in a plane perpendicular to said axis of symmetry, while detecting by said radiation detector, to obtain tomosynthesis data of said object; and said divergent radiation source and said radiation detector are moved relative said object linearly along said second axis a distance corresponding to a distance between two adjacent detectors in a column of said two-dimensional array, while detecting by said radiation detector, to obtain still picture data of said object.

40. An apparatus for obtaining tomographic and tomosynthesis data of an object comprising:

a divergent radiation source provided for emitting radiation centered around an axis of symmetry;

a radiation detector comprising a two-dimensional array of line detectors, each having a detection-sensitive area directed towards the divergent radiation source and being provided for one-dimensional imaging of radiation entering said detection-sensitive area;

a region arranged in the radiation path between said divergent radiation source and said radiation detector provided for housing said object; and a device provided for moving said divergent radiation source and said radiation detector relative said object, while each of said line detectors is adapted to record a plurality of line images of radiation as transmitted through said object, wherein:

said divergent radiation source is provided for emitting radiation within a solid angle such that radiation is directed towards the full extension of said object at least in a first dimension, which is perpendicular to said axis of symmetry;

the line detectors of said two-dimensional array of line detectors are sited in rows and columns, wherein the line detectors of each row are sited edge-to-edge along a line, and are of a number and have each a length such that they are together capable of detecting said radiation directed towards the full extension of said object in said first dimension; and said moving device is provided for
 moving said divergent radiation source and said radiation detector relative said object helically around a second axis being essentially perpendicular to said axis of symmetry and the direction of said first dimension, to obtain tomographic data of said object; and
 moving said divergent radiation source and said radiation detector relative said object linearly in a plane perpendicular to said axis of symmetry to obtain tomosynthesis data of said object.

41. An apparatus for obtaining tomographic and still picture data of an object comprising:

a divergent radiation source provided for emitting radiation centered around an axis of symmetry;

a radiation detector comprising a two-dimensional array of line detectors, each having a detection-sensitive area directed towards the divergent radiation source and being provided for one-dimensional imaging of radiation entering said detection-sensitive area;

a region arranged in the radiation path between said divergent radiation source and said radiation detector provided for housing said object; and a device provided for moving said divergent radiation source and said radiation detector relative said object, while each of said line detectors is adapted to record a plurality of line images of radiation as transmitted through said object, wherein:

said divergent radiation source is provided for emitting radiation within a solid angle such that radiation is directed towards the full extension of said object at least in a first dimension, which is perpendicular to said axis of symmetry;

the line detectors of said two-dimensional array of line detectors are sited in rows and columns, wherein the line detectors of each row are sited edge-to-edge along a line, and are of a number and have each a length such that they are together capable of detecting said radiation directed towards the full extension of said object in said first dimension; and said moving device is provided for
 moving said divergent radiation source and said radiation detector relative said object helically around a second axis being essentially perpendicular to said axis of symmetry and the direction of said first dimension, to obtain tomographic data of said object; and
 moving said divergent radiation source and said radiation detector relative said object linearly along said second axis a distance corresponding to a distance between two adjacent detectors in a column of said two-dimensional array to obtain still picture data of said object.

42. An apparatus for obtaining tomographic data of an object comprising:

a divergent radiation source provided for emitting radiation centered around an axis of symmetry;

a radiation detector comprising a two-dimensional array of line detectors, each having a detection-sensitive area directed towards the divergent radiation source and being provided for one-dimensional imaging of radiation entering said detection-sensitive area;

a region arranged in the radiation path between said divergent radiation source and said radiation detector provided for housing said object; and a device provided for moving said divergent radiation source and said radiation detector relative said object, while each of said line detectors is adapted to record a plurality of line images of radiation as transmitted through said object, wherein:

said divergent radiation source is provided for emitting radiation within a solid angle such that radiation is directed towards the full extension of said object at least in a first dimension, which is perpendicular to said axis of symmetry;

the line detectors of said two-dimensional array of line detectors are sited in rows and columns, wherein the line detectors of each row are sited edge-to-edge along a line, and are of a number and have each a length such that they together define an opening angle large enough to detect said radiation directed towards the full extension of said object in said first dimension; and said moving device is provided for moving said divergent radiation source and said radiation detector relative said object helically around a second axis being essentially perpendicular to said axis of symmetry and the direction of said first dimension, to obtain tomographic data of said object, wherein said helical movement includes a rotation of at least the sum of a half revolution and said opening angle, and a distance along said second axis corresponding at least to a distance between two adjacent detectors in a column of said two-dimensional array.

43. The apparatus of claim 42 wherein said helical movement includes a rotation of at least the sum of two full revolutions and said opening angle.

44. The apparatus of claim 42 wherein said helical movement includes a rotation, which corresponds to a predetermined required spatial resolution in an image reconstructed from said tomographic data.

* * * * *